United States Patent

Achhammer et al.

[11] Patent Number: 6,147,208
[45] Date of Patent: Nov. 14, 2000

[54] PROCESS FOR SIMULTANEOUSLY PREPARING CAPROLACTAM AND HEXAMETHYLENE DIAMINE

[75] Inventors: Günther Achhammer, Mannheim; Peter Bassler, Viernheim; Rolf Fischer, Heidelberg; Eberhard Fuchs, Frankenthal; Hermann Luyken, Ludwigshafen; Werner Schnurr, Herxheim; Guido Voit, Schriesheim; Lutz Hilprecht, Ludwigshafen, all of Germany

[73] Assignee: BASF Aktiengesellschaft, Ludwigshafen, Germany

[21] Appl. No.: 09/091,130
[22] PCT Filed: Dec. 11, 1996
[86] PCT No.: PCT/EP96/05521
  § 371 Date: Jun. 16, 1998
  § 102(e) Date: Jun. 16, 1998
[87] PCT Pub. No.: WO97/23454
  PCT Pub. Date: Jul. 3, 1997

[30] Foreign Application Priority Data

Dec. 22, 1995 [DE] Germany .............. 195 48 289

[51] Int. Cl.$^7$ .......................... C07D 201/02; C07C 211/12
[52] U.S. Cl. ................................. 540/538; 564/511
[58] Field of Search ..................... 540/538, 540; 564/511

[56] References Cited

U.S. PATENT DOCUMENTS

| | | | |
|---|---|---|---|
| 2,208,598 | 7/1940 | Rigby | 260/464 |
| 2,257,814 | 10/1941 | Rigby | 260/464 |
| 2,301,964 | 11/1942 | Martin | 260/239 |
| 2,357,484 | 9/1944 | Martin | 260/239 |
| 2,762,835 | 9/1956 | Swerdloff | 260/465.5 |
| 3,862,911 | 1/1975 | Chabert | 252/470 |
| 4,601,859 | 7/1986 | Galle et al. | 558/459 |

FOREIGN PATENT DOCUMENTS

| | | |
|---|---|---|
| 150295 | 8/1985 | European Pat. Off. . |
| 2029540 | 10/1970 | France . |
| 848654 | 7/1949 | Germany . |
| 954416 | 12/1956 | Germany . |
| 4235466 | 4/1994 | Germany . |
| 4319134 | 12/1994 | Germany . |
| 92/21650 | 12/1992 | WIPO . |

OTHER PUBLICATIONS

Appl. Het. Cat., 1987, pp. 106–122.
Catalysis, vol. 4, 1981, pp. 1–30.
Bull. Soc. Chem., 13, 1946, p. 208.
J. Chem. Soc., Faraday Trans. vol. 89, No. 18, 1993, pp. 3507–3512.
Chem. Abst., vol. 82, No. 10., 1975.

Primary Examiner—Joseph K. McKane
Assistant Examiner—Dominic Keating
Attorney, Agent, or Firm—Keil & Weinkauf

[57] ABSTRACT

Caprolactam and hexamethylenediamine are prepared simultaneously starting from adiponitrile.

9 Claims, 1 Drawing Sheet

PROCESS FOR SIMULTANEOUSLY PREPARING CAPROLACTAM AND HEXAMETHYLENE DIAMINE

Figure 1:
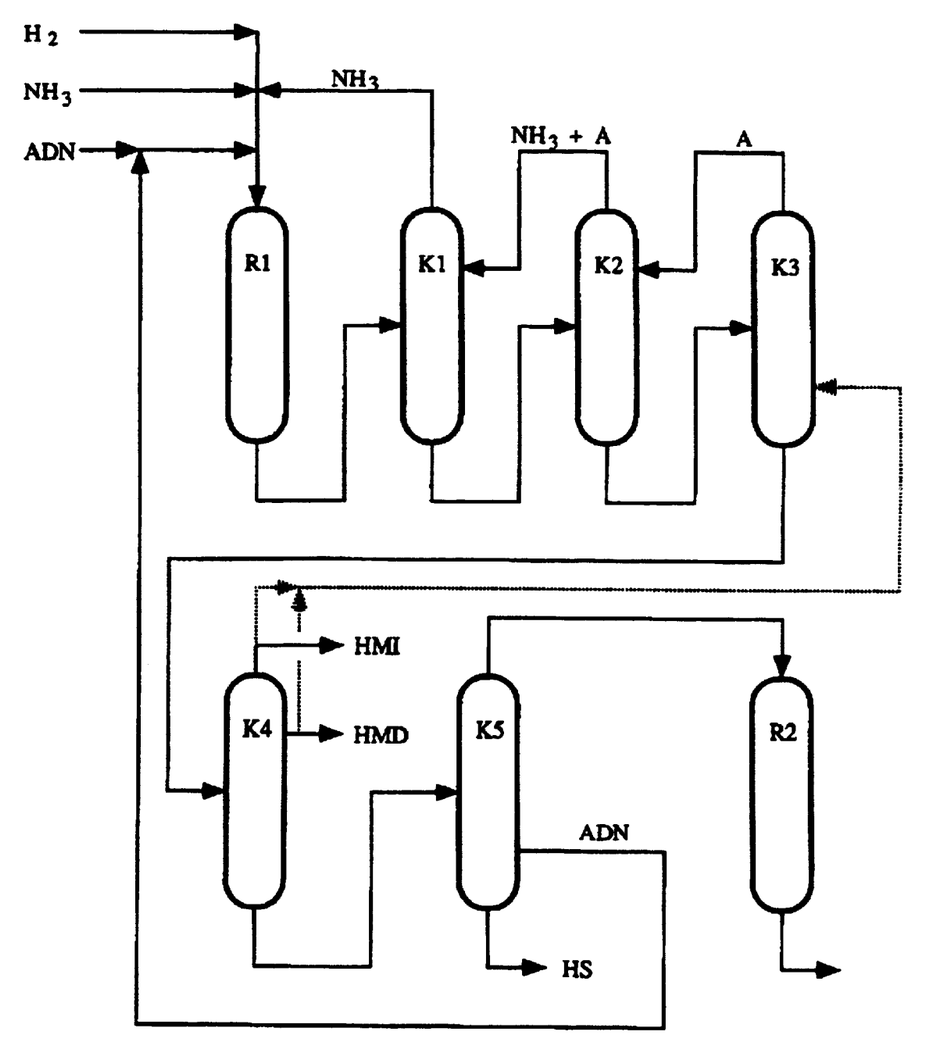

This application is a 371 of PCT/EP96/05521, filed Dec. 11, 1996.

The present invention relates to a process for the simultaneous preparation of caprolactam and hexamethylenediamine starting from adiponitrile.

The present invention furthermore relates to an improved process for the simultaneous separation of 6-aminocapronitrile and hexamethylenediamine from a mixture containing these substances. The partial hydrogenation of adiponitrile to 6-aminocapronitrile in the presence of ammonia and various catalysts has been sufficiently described. For example, U.S. Pat. No. 4,601,859 describes the use of catalysts based on rhodium on magnesium oxide, U.S. Pat. No. 2,762,835 describes the use of Raney nickel, U.S. Pat. No. 2,208,598 describes the use of nickel on alumina, DE-A 848 654 describes fixed-bed catalysts based on copper/cobalt/zinc and iron/cobalt spinels, DE-A 954 416 describes the use of cobalt on silica gel and DE-A 4 235 466 describes the use of iron sponges.

In the process described in WO 92/21650, aminocapronitrile yields of 60% at a conversion of 70% and hexamethylenediamine yields of 9% are achieved in the presence of Raney nickel. At a conversion of 80%, the yield is 62%.

It is also known that 6-aminocapronitrile can be reacted with water in the gas or liquid phase in the presence or absence of catalysts with liberation of ammonia to give caprolactam. For example, U.S. Pat. No. 2,301,964 describes a process in which from 10 to 25% strength solutions of 6-aminocapronitrile are converted in the liquid phase at from 250 to 290° C. into caprolactam in yields of up to 76%.

Furthermore, the cyclization of from 25 to 35% strength 6-aminocapronitrile solutions at 220° C. in the liquid phase in water with the addition of organic solvents in the presence of zinc compounds, copper compounds, lead compounds and mercury compounds is described in FR-A 2,029,540. Caprolactam yields of up to 83% are achieved here.

The cyclization of 6-aminocapronitrile can also be carried out in the gas phase (U.S. Pat. No. 2,357,484): starting from 80% strength aqueous solutions, caprolactam yields of 92% are achieved at 305° C. using alumina as a catalyst.

EP-A 150 295 describes the reaction of 6-aminocapronitrile in the gas phase in the presence of copper/vanadium catalysts, hydrogen, water and ammonia at 290° C. with a 77% yield of caprolactam.

Furthermore, DE-A 43 19 134 describes the conversion of 6-aminocapronitrile into caprolactam in water in the liquid phase without the addition of a catalyst.

The abovementioned documents do not suggest a process by means of which caprolactam is obtained from adiponitrile via 6-aminocapronitrile in an overall process comprising both process steps.

It is an object of the present invention to provide a process for the simultaneous preparation of caprolactam and hexamethylenediamine starting from adiponitrile. Furthermore, it was intended to provide a process which gives pure 6-aminocapronitrile and hexamethylenediamine in a continuous process from the reaction mixture obtained in the partial hydrogenation of adiponitrile, the 6-aminocapronitrile being cyclized to caprolactam in a further process step. Moreover, byproducts obtained in this process were as far as possible to be reused, preferably recycled to an earlier process stage.

We have found that this object is achieved by a process for the simultaneous preparation of caprolactam and hexamethylenediamine starting from adiponitrile, wherein (a) adiponitrile is partially hydrogenated to give a mixture containing essentially 6-aminocapronitrile, hexamethylenediamine, ammonia, adiponitrile and hexamethyleneimine, and (b) the mixture obtained in (a) is subjected to a distillation to give ammonia as the top product and a bottom product I, the distillation being carried out at a bottom temperature of from 60 to 250° C. and a pressure of from 5 to 30 bar in the presence of a compound A which is inert under the distillation conditions, or a mixture of inert compounds A, which boils at from 60 to 250° C. at 18 bar, and the ammonia not being completely separated off, and (c) the bottom product I, containing essentially 6-aminocapronitrile, hexamethylenediamine, adiponitrile, hexamethyleneimine, inert compound or compounds A and ammonia, the ammonia content being lower than that of the mixture used in stage (b), is subjected to a second distillation to give a mixture of the inert compound A and ammonia as the top product and a bottom product II, the distillation being carried out at a bottom temperature of from 100 to 250° C. and a pressure of from 2 to 15 bar, with the proviso that the pressures of the first and of the second column are matched with one another so that, at a bottom temperature of not more than 250° C. in each case, a top temperature of more than 20° C. is obtained, or, in the condenser thereof, the condensation at the top of the second column is carried out at lower temperatures, the top product, which consists of pure or relatively highly concentrated ammonia, being recycled to the first column, or the top product of the second column is recycled to the first column or to the condenser thereof in vapor form after the pressure has been increased by means of a compressor, (d) the bottom product II, containing essentially 6-aminocapronitrile, hexamethylenediamine, adiponitrile, hexamethyleneimine and inert compound or compounds A, is subjected to a distillation in a third column to give the inert compound or compounds A as the top product and a bottom product III, the distillation being carried out at a bottom temperature of from 50 to 250° C. and a pressure of from 0.05 to 2 bar, with the proviso that the inert compounds A obtained as the top product are fed to the second column, and, if desired, the distillation being carried out in the presence of one or more compounds B which are inert under the distillation conditions and boil at from 20 to 250° C. at 0.3 bar, (e) the bottom product III, containing essentially 6-aminocapronitrile, hexamethylenediamine, adiponitrile, hexamethyleneimine and, if desired, inert compound or compounds B, is subjected to distillation in a fourth column to give a top product KP1, containing essentially hexamethyleneimine, if desired inert compound or compounds B, and a side stream SA1, containing essentially hexamethylenediamine, the bottom temperature of the column being from 50 to 250° C. and the pressure from 0.05 to 1.5 bar, and to give a bottom product IV, and, if desired, the column is equipped with a dividing wall in the region between feed and side take-off point (Petyuk [sic] column), so that the hexamethylenediamine obtained is essentially free of hexamethyleneimine and inert compound or compounds B and of other low boilers, top product KP1 being fed to the third column or, if required, only some of top product KP1 being fed to the third column and the remainder being removed, and (f) the bottom product IV, containing essentially 6-aminocapronitrile and adiponitrile and possibly high boilers, is subjected to a distillation in a fifth column to give 6-aminocapronitrile having a purity of at least 95% as the top product and a side stream consisting essentially of adiponitrile and a bottom product V which consists of high boilers and small amounts of adiponitrile, and, if desired, the column is equipped with a dividing wall in the region between feed and side take-off point, so that the adiponitrile obtained contains relatively small amounts of high boilers, the distillation being carried out at a bottom temperature of from 50 to 250° C. and a pressure of from 10 to 300 mbar, and the 6-aminocapronitrile thus obtained is then cyclized to give caprolactam.

We have also found a process for the simultaneous separation of 6-aminocapronitrile and hexamethylenediamine from a mixture containing these substances.

The partial hydrogenation of adiponitrile can be carried out by one of the known processes, for example by one of the abovementioned processes described in U.S. Pat. No. 4,601,859, U.S. Pat. No. 2,762,835, U.S. Pat. No. 2,208,598, DE-A 848 654, DE-A 954 416, DE-A 4 235 466 or WO 92/21650, by effecting the hydrogenation in general in the presence of nickel-, cobalt-, iron- or rhodium-containing catalysts. The catalysts may be used in the form of supported catalysts or unsupported catalysts. Examples of suitable catalyst carriers are alumina, silica, titanium dioxide, magnesium oxide, active carbons and spinels. Examples of suitable unsupported catalysts are Raney nickel and Raney cobalt.

The catalyst space velocity is usually chosen in the range from 0.05 to 10, preferably from 0.1 to 5, kg of adiponitrile per 1 of catalyst per hour.

Hydrogenation is carried out, as a rule, at from 20 to 200° C., preferably from 50 to 150° C., and at hydrogen partial pressures of from 0.1 to 20, preferably from 0.5 to 10, MPa.

The hydrogenation is preferably carried out in the presence of a solvent, in particular ammonia. The amount of ammonia is chosen in general in the range from 0.1 to 10, preferably from 0.5 to 3, kg of ammonia per kg of adiponitrile.

The molar ratio of 6-aminocapronitrile to hexamethylenediamine and hence the molar ratio of caprolactam to hexamethylenediamine can be controlled by the adiponitrile conversion chosen in each case. Adiponitrile conversions of from 10 to 90%, preferably from 30 to 80%, are preferably employed in order to obtain high 6-aminocapronitrile selectivities.

As a rule, the sum of 6-aminocapronitrile and hexamethylenediamine is from 95 to 99%, depending on the catalyst and reaction conditions, hexamethyleneimine being the most important byproduct in terms of quantity.

In a preferred embodiment, the reaction is carried out in the presence of ammonia and lithium hydroxide or a lithium compound which forms lithium hydroxide under the reaction conditions, at from 40 to 120° C., preferably from 50 to 100° C., particularly preferably from 60 to 90° C.; the pressure is chosen in general in the range from 2 to 12, preferably from 3 to 10, particularly preferably from 4 to 8, MPa. The residence times are essentially dependent on the desired yield, the selectivity and the desired conversion; usually, the residence time is chosen so that a maximum yield is achieved, for example in the range from 50 to 275, preferably from 70 to 200, minutes.

The pressure and temperature ranges are preferably chosen so that the reaction can be carried out in the liquid phase.

Ammonia is used in general in an amount such that the weight ratio of ammonia to dinitrile is from 9:1 to 0.1:1, preferably from 2.3:1 to 0.25:1, particularly preferably from 1.5:1 to 0.4:1.

The amount of lithium hydroxide is chosen as a rule in the range from 0.1 to 20, preferably from 1 to 10, % by weight, based on the amount of catalyst used.

Examples of lithium compounds which form lithium hydroxide under the reaction conditions are lithium metal and alkyllithium and aryllithium compounds such as n-butyllithium and phenyllithium. The amount of these compounds is chosen in general so that the abovementioned amount of lithium hydroxide is obtained.

Preferably used catalysts are nickel-, ruthenium-, rhodium-, iron- and cobalt-containing compounds, preferably those of the Raney type, in particular Raney nickel and Raney cobalt. The catalysts may also be used in the form of supported catalysts, carriers which may be used being, for example, alumina, silica, zinc oxide, active carbon and titanium dioxide (cf. Appl. Het. Cat. (1987), 106–122; Catalysis 4 (1981), 1–30). Raney nickel (for example from BASF AG, Degussa and Grace) is particularly preferred.

The nickel-, ruthenium-, rhodium-, iron- and cobalt-catalysts may be modified with metals of groups VIB (Cr, Ho, W) and VIII (Fe, Ru, Os, Co (only in the case of nickel), Rh, Ir, Pd, Pt) of the Periodic Table. Observations to date have shown that the use of, in particular, modified Raney nickel catalysts, for example modified with chromium and/or iron, leads to higher aminonitrile selectivities (for preparation, cf. DE-A 2 260 978 and Bull. Soc. Chem. 13 (1946), 208).

The amount of catalyst is chosen in general so that the amount of cobalt, ruthenium, rhodium, iron or nickel is from 1 to 50, preferably from 5 to 20, % by weight, based on the amount of dinitrile used.

The catalysts may be used as fixed-bed catalysts by the liquid phase or trickle-bed procedure or as suspended catalysts.

In a further preferred embodiment, adiponitrile is partially hydrogenated to 6-aminocapronitrile at elevated temperatures and high pressure in the presence of a solvent and of a catalyst by using a catalyst which (a) contains a compound based on a metal selected from the group consisting of nickel, cobalt, iron, ruthenium and rhodium and (b) from 0.01 to 25, preferably from 0.1 to 5, % by weight, based on (a), of a promoter based on a metal selected from the group consisting of palladium, platinum, iridium, osmium, copper, silver, gold, chromium, molybdenum, tungsten, manganese, rhenium, zinc, cadmium, lead, aluminum, tin, phosphorus, arsenic, antimony, bismuth and rare earth metals, and (c) from 0 to 5, preferably from 0.1 to 3, % by weight, based on (a), of a compound based on an alkali metal or an alkaline earth metal, with the proviso that, if a compound based on only ruthenium or rhodium or ruthenium and rhodium or nickel and rhodium is chosen as component (a), the promoter (b) can, if desired, be dispensed with.

Preferred catalysts are those in which the component (a) contains at least one compound based on a metal selected from the group consisting of nickel, cobalt and iron, in an amount of from 10 to 95% by weight and ruthenium and/or rhodium in an amount of from 0.1 to 5% by weight, based in each case on the sum of components (a) to (c), component (b) contains at least one promoter based on a metal selected from the group consisting of silver, copper, manganese, rhenium, lead and phosphorus, in an amount of from 0.1 to 5% by weight, based on (a), and component (c) contains at least one compound based on the alkali metals and alkaline earth metals, selected from the group consisting of lithium, sodium, potassium, cesium, magnesium and calcium, in an amount of from 0.1 to 5% by weight.

Particularly preferred catalysts are:

catalyst A, containing 90% by weight of cobalt oxide (CoO), 5% by weight of manganese oxide ($Mn_2O_3$), 3% by weight of phosphorus pentoxide and 2% by weight of sodium oxide ($Na_2O$), catalyst B, containing 20% by weight of cobalt oxide (CoO), 5% by weight of manganese oxide ($Mn_2O_3$), 0.3% by weight of silver oxide ($Al_2O$), 70% by weight of silica ($SiO_2$), 3.5% by weight of alumina ($Al_2O_3$), 0.4% by weight of iron oxide ($Fe_2O_3$), 0.4% by weight of magnesium oxide (MgO) and 0.4% by weight of calcium oxide (CaO), and catalyst C, containing 20% by weight of nickel oxide (NiO), 67.42% by weight of silica ($SiO_2$), 3.7% by weight of alumina ($Al_2O_3$), 0.8% by weight of iron oxide ($Fe_2O_3$), 0.76% by weight of magnesium oxide (MgO), 1.92% by weight of calcium oxide (CaO), 3.4% by weight of sodium oxide ($Na_2O$) and 2.0% by weight of potassium oxide ($K_2O$).

The catalysts which may be preferably used may be unsupported catalysts or supported catalysts. Examples of suitable carrier materials are porous oxides, such as alumina, silica, aluminosilicates, lanthanum oxide, titanium dioxide, zirconium dioxide, magnesium oxide, zinc oxide and zeolites, and active carbon or mixtures thereof.

The preparation is carried out as a rule by a procedure in which precursors of the components (a) are precipitated together with precursors of the promoters (components (b) and, if desired, with precursors of the trace components (c) in the presence or absence of carrier materials (depending on the catalyst type desired), if desired the resulting catalyst precursor is processed to give extrudates or pellets and is dried and then calcined. Supported catalysts are generally also obtainable by impregnating the carrier with a solution of the components (a), (b) and, if desired, (c), it being possible to add the individual components simultaneously or in succession, or by spraying the components (a), (b) and, if desired, (c) onto the carrier by a method known per se.

Suitable precursors of the components (a) are as a rule readily water-soluble salts of the abovementioned metals, such as nitrates, chlorides, acetates, formates and sulfates, preferably nitrates.

Suitable precursors of the components (b) are as a rule readily water-soluble salts or complex salts of the abovementioned metals, such as nitrates, chlorides, acetates, formates and sulfates and in particular hexachloroplatinate, preferably nitrates and hexachloroplatinate.

Suitable precursors of the components (c) are as a rule readily water-soluble salts of the abovementioned alkali metals and alkaline earth metals, such as hydroxides, carbonates, nitrates, chlorides, acetates, formates and sulfates, preferably hydroxides and carbonates.

The precipitation is generally effected from aqueous solutions, alternatively by adding precipitating reagents, by changing the pH or by changing the temperature.

The catalyst precursor thus obtained is usually dried, generally at from 80 to 150° C., preferably from 80 to 120° C.

The calcination is usually carried out at from 150 to 500° C., preferably from 200 to 450° C., in a gas stream comprising air or nitrogen.

After calcination, the catalyst material obtained is generally exposed to a reducing atmosphere (activation), for example by exposing it for from 2 to 24 hours to a hydrogen atmosphere or a gas mixture containing hydrogen and an inert gas, such as nitrogen, at from 80 to 250° C., preferably from 80 to 180° C., in the case of catalysts based on ruthenium or rhodium as component (a) or at from 200 to 500° C., preferably from 250 to 400° C., in the case of catalysts based on one of the metals selected from the group consisting of nickel, cobalt and iron as component (a). The catalyst loading here is preferably 200 l per l of catalyst.

Advantageously, the activation of the catalyst is carried out directly in the synthesis reactor, since this usually dispenses with an otherwise necessary intermediate step, i.e. the passivation of the surface, usually at from 20 to 80° C., preferably from 25 to 35° C., by means of oxygen/nitrogen mixtures, such as air. The activation of passivated catalysts is then preferably carried out in the synthesis reactor at from 180 to 500° C., preferably from 200 to 350° C., in a hydrogen-containing atmosphere.

The catalysts may be used as fixed-bed catalysts by the liquid phase or trickle-bed procedure or as suspended catalysts.

If the reaction is carried out in a suspension, temperatures of from 40 to 150° C., preferably from 50 to 100° C., particularly preferably from 60 to 90° C., are usually chosen; the pressure is chosen in general in the range from 2 to 20, preferably from 3 to 10, particularly preferably from 4 to 9, MPa. The residence times are essentially dependent on the desired yield, the selectivity and the desired conversion; usually, the residence time is chosen so that a maximum yield is achieved, for example in the range from 50 to 275, preferably from 70 to 200, minutes.

In the suspension procedure, preferably used solvents are ammonia, amines, diamines and triamines of 1 to 6 carbon atoms, such as trimethylamine, triethylamine, tripropylamine and tritutylamine, or alcohols, in particular methanol and ethanol, particularly preferably ammonia. A dinitrile concentration of from 10 to 90, preferably from 30 to 80, particularly preferably from 40 to 70, % by weight, based on the sum of dinitrile and solvent, is advantageously chosen.

The amount of catalyst is chosen in general in the range from 1 to 50, preferably from 5 to 20, % by weight, based on the amount of dinitrile used.

The suspension hydrogenation may be carried out batchwise or, preferably, continuously, as a rule in the liquid phase.

The partial hydrogenation can also be carried out batchwise or continuously in a fixed-bed reactor by the trickle-bed or liquid phase procedure, a temperature of from 20 to 150° C., preferably from 30 to 90° C., and a pressure of, as a rule, from 2 to 30, preferably from 3 to 20, MPa usually being chosen. The partial hydrogenation is preferably carried out in the presence of a solvent, preferably ammonia, an amine, a diamine or a triamine of 1 to 6 carbon atoms, such as trimethylamine, triethylamine, tripropylamine or tributylamine, or an alcohol, preferably methanol or ethanol, particularly preferably ammonia. In a preferred embodiment, an ammonia content of from 1 to 10, preferably from 2 to 6, g per g of adiponitrile is chosen. A catalyst space velocity of from 0.1 to 2.0, preferably from 0.3 to 1.0, kg of adiponitrile per 1 per h is preferably chosen. Here too, the conversion and hence the selectivity can be controlled by changing the residence time.

The partial hydrogenation can be carried out in a conventional reactor suitable for this purpose (R1 in the drawing).

The distillation in the first column (stage (b); K1 in the drawing) is carried out according to the invention by a method in which the mixture from stage (a), containing essentially 6-aminocapronitrile, hexamethylenediamine, ammonia, adiponitrile and hexamethyleneimine, preferably a mixture containing essentially from 1 to 70, preferably from 5 to 40, % by weight of 6-aminocapronitrile, from 1 to 70, preferably from 5 to 40, % by weight of adiponitrile, from 0.1 to 70, preferably from 1 to 40, % by weight of hexamethylenediamine, from 0.01 to 10, preferably from 0.05 to 5, % by weight of hexamethyleneimine and from 5 to 95, preferably from 20 to 85, % by weight of ammonia, is carried out as a rule in a conventional distillation column at a bottom temperature of from 60 to 250° C., preferably from 100 to 200° C., and a pressure of from 5 to 30, preferably from 12 to 25, bar in the presence of one or more compounds A which are inert under the distillation conditions and boil at from 60 to 220° C. at 18 bar, to give ammonia as the top product and a bottom product I, the ammonia not being completely separated off.

According to the invention, suitable compounds A are substances which are inert under the distillation conditions and have a boiling point of from 60 to 250° C., preferably from 60 to 150° C., at 18 bar. Examples are alkanes, cycloalkanes, aromatics, naphthenes, alcohols, ethers, nitrites and amines having the abovementioned properties, in particular $C_5$–$C_8$-alkanes and $C_2$–$C_4$-alkanols, particularly preferably n-pentane, cyclohexane, triethylamine, ethanol, acetonitrile, n-hexane, di-n-propyl ether, isopropanol, n-butylamine and benzene, very particularly preferably ethanol.

Compound A is usually added in an amount of from 0.1 to 50, preferably from 1 to 10, % by weight, based on the bottom product In stage (c), the bottom product I, containing essentially 6-aminocapronitrile, hexamethylenediamine, adiponitrile, hexamethyleneimine, inert compound or compounds A and ammonia, the ammonia content being lower than that of the mixture obtained from stage (a) and used in stage (b), is subjected to a second distillation to give a mixture of the inert compound or compounds A and ammonia as the top product and a bottom product II, the distillation being carried out at a bottom temperature of from 100 to 250° C., preferably from 140 to 200° C., and at from 2 to 15, preferably from 4 to 12, bar, with the proviso that the pressures of the first and of the second column (K2 in the drawing) are matched with one another so that a top temperature of more than 20° C. is obtained at a respective bottom temperature of not more than 250° C. It may also be advantageous to carry out the condensation at the top of the second column at lower temperatures, the top product, which consists of pure or relatively highly concentrated ammonia, being recycled to the first column, or to recycle the top product of the second column in vapor form, after increasing the pressure by means of a compressor, to the first column or to its condenser.

In stage (d), the bottom product II, containing essentially 6-aminocapronitrile, hexamethylenediamine, adiponitrile, hexamethyleneimine and inert compound or compounds A, is subjected to a distillation in a third column (K3 in the drawing) to give the inert compound or compounds A as the top product and a bottom product III, the distillation being carried out at a bottom temperature of from 50 to 250° C., preferably from 140 to 200° C., and at from 0.05 to 2, preferably from 0.2 to 1, bar, with the proviso that the inert compound or compounds A obtained as the top product is or are fed to the second column, and, if desired, the distillation is carried out in the presence of one or more compounds B which are inert under the distillation conditions and boil at from 20 to 250° C., preferably from 60 to 170° C., at a given pressure of 0.3 bar.

Examples of compounds B are alkanes, cycloalkanes, aromatics, naphthenes, alcohols, ethers, nitrites and amines having the abovementioned properties, in particular di-n-butyl ether, valeronitrile, n-octane, cyclooctane, n-hexylamine, hexamethyleneimine and hexamethylenediamine, preferably hexamethyleneimine and/or hexamethylenediamine, particularly preferably hexamethyleneimine.

In a preferred embodiment, hexamethyleneimine and/or hexamethylenediamine are chosen as compound B or, particularly preferably, no further compound B is added.

Compound B is preferably added to the column K3 in an amount of from 0.01 to 50, preferably from 0.5 to 10, % by weight, based on the bottom product II.

In stage (e), the bottom product III, containing essentially 6-aminocapronitrile, hexamethylenediamine, adiponitrile, hexamethyleneimine and, if desired, inert compound or compounds B, is subjected to a distillation in a fourth column (K4 in the drawing) to give a top product KP1, containing essentially hexamethyleneimine, if desired inert compound or compounds B and a side stream SA1, containing essentially hexamethylenediamine, the bottom temperature of the column being from 50 to 250° C. and the pressure from 0.05 to 1.5 bar, and to give a bottom product IV.

If desired, the column is equipped with a dividing wall in the region between feed and side take-off point (Petlyuk column) so that the hexamethylenediamine obtained is essentially free of hexamethyleneimine and inert compound or compounds B and of other low boilers, top product KP1 and/or HMD from the side stream SA1 being fed, if required, to the third column or, if required, only a part thereof being fed to the third column and the remainder being removed.

In stage (f), the bottom product IV, containing essentially 6-aminocapronitrile and adiponitrile and possibly high boilers, is subjected to a distillation in a fifth column (K5 in the drawing) to give 6-aminocapronitrile having a purity of at least 95%, preferably from 99 to 99.9%, as the top product and a side stream consisting essentially of adiponitrile and a bottom product V which consists of high boilers and small amounts of adiponitrile.

If desired, the column is equipped with a dividing wall in the region between feed and side take-off point, so that the adiponitrile obtained contains relatively small amounts of high boilers, the distillation being carried out at a bottom temperature of from 50 to 250° C. and at from 10 to 300 mbar.

Adiponitrile (ADN) from side stream 2 (SA2) is recycled to the reactor R1.

According to the invention, the 6-aminocapronitrile obtained is converted into caprolactam. This cyclization can be carried out by known processes in the liquid or gas phase, for example by a process disclosed in U.S. Pat. No. 2,301,964, U.S. Pat. No. 2,357,484, EP-A 150 295 or DE-A 43 19 134, usually by reacting the 6-aminocapronitrile with water in the liquid phase to give caprolactam and ammonia.

In the reaction without a catalyst, a temperature of from 200 to 375° C. and reaction times of from 10 to 90, preferably from 10 to 30, minutes are chosen. As a rule, water is used as the solvent, the 6-aminocapronitrile content generally being chosen in the range of less than 30, preferably from 10 to 25, % by weight, based on the water.

In the reaction in the liquid phase in the presence of a catalyst, a temperature of from 50 to 330° C., an amount of water of from 1.3 to 50, preferably from 1.3 to 30, mol per mol of 6-aininocapronitrile and a reaction time of from 10 minutes to several hours are usually chosen. When an organic solvent is used, in particular an alcohol, the amount of water generally chosen is from 1.3 to 5 mol per mol of 6-aminocapronitrile.

The reacted mixture obtained in the cyclization is usually first worked up by distillation, ammonia, water and any organic solvent being separated off. If a catalyst is used, the catalyst present in the bottom product is generally separated from the caprolactam by one of the conventional methods and recycled to the cyclization reactor (R2 in the drawing). The crude caprolactam is generally converted into pure lactam by purification operations known per se, such as distillation, and is then available for polymerization to polycaprolactam.

In a preferred embodiment, 6-aminocapronitrile is reacted with water in the liquid phase with the use of heterogeneous catalysts.

The reaction is carried out in the liquid phase at in general from 140 to 320° C., preferably from 160 to 280° C.; the pressure is in general from 1 to 250, preferably from 5 to 150, bar, and it should be ensured that the reaction mixture is predominantly liquid under the conditions used. The residence times are in gereral from 1 to 120, preferably from 1 to 90, in particular from 1 to 60, minutes. In some cases, residence times of from 1 to 10 minutes have proven completely sufficient.

In general, at least 0.01, preferably from 0.1 to 20, in particular from 1 to 5, mol of water are used per mol of 6-aminocapronitrile.

Advantageously, the 6-aminocapronitrile is used in the form of a 1–50, in particular 5–50, particularly preferably 5–30, % strength by weight solution in water (in which case the solvent is simultaneously a reactant) or in water/solvent mixtures. Examples of solvents are alkanols, such as methanol, ethanol, n-propanol, isopropanol, n-butanol, isobutanol and tert-butanol, and polyols such as diethylene glycol and tetraethylene glycol, hydrocarbons such as petroleum ether, benzene, toluene and xylene, lactams, such as pyrrolidone and caprolactam, and alkyl-substituted lactams, such as N-methylpyrrolidone, N-methylcaprolactam and N-ethylcaprolactam, and carboxylates, preferably of carboxylic acids of 1 to 8 carbon atoms. Ammonia may also be present in the reaction. Mixtures of organic solvents may of course also be used. Mixtures of water and alkanols in a water/alkanol weight ratio of 1–75/25–99, preferably 1–50/50–99, have proven particularly advantageous in some cases.

It is in principle just as possible to use the 6-aminocapronitrile as a reactant and simultaneously as a solvent.

Examples of heterogeneous catalysts which may be used are:

acidic, basic or amphoteric oxides of the elements of the second, third or fourth main group of the Periodic Table, such as calcium oxide, magnesium oxide, boron oxide, alumina, tin oxide or silica in the form of pyrogenic silica, silica gel, kieselguhr, quartz or mixtures thereof, and oxides of metals of the second to sixth subgroups of the Periodic Table, such as titanium oxide, in amorphous form or as anatase or rutile, zirconium oxide, zinc oxide, manganese oxide or mixtures thereof. Oxides of the lanthanides and actinides, such as cerium oxide, thorium oxide, praseodymium oxide and samarium oxide, rare earth mixed oxide and mixtures thereof with the abovementioned oxides may also be used. Examples of further catalysts are:

vanadium oxide, niobium oxide, iron oxide, chromium oxide, molybdenum oxide, tungsten oxide and mixtures thereof. Mixtures of the stated oxides with one another are also possible. Some sulfides, selenides and tellurides, such as zinc telluride, tin selenide, molybdenum sulfide, tungsten sulfide and sulfides of nickel, of zinc and of chromium, may also be used.

The abovementioned compounds may be doped with compounds of main groups 1 and 7 of the Periodic Table or may contain these compounds.

Furthermore, zeolites, phosphates and heteropolyacids and acidic and alkaline ion exchangers, for example Naphion®, are examples of suitable catalysts.

If required, these catalysts may contain up to 50% by weight in each case of copper, tin, zinc, manganese, iron, cobalt, nickel, ruthenium, palladium, platinum, silver or rhodium.

Depending on the composition of the catalyst, the catalysts may be used as unsupported catalysts or supported catalysts. For example, titanium dioxide may be used as titanium dioxide extrudates or as titanium dioxide applied in a thin layer on a carrier. All methods described in the literature may be used for applying titanium dioxide to a carrier such as silica, alumina or zirconium dioxide. Thus, a thin titanium dioxide layer can be applied by hydrolysis of titanium organyls, such as titanium isopropylate or titanium butylate, or by hydrolysis of $TiCl_4$ or other inorganic titanium-containing compounds. Sols containing titanium dioxide may also be used.

Further suitable compounds are zirconyl chloride, aluminum nitrate and cerium nitrate.

Suitable carriers are powders, extrudates or pellets of the stated oxides themselves or of other stable oxides, such as silica. The carriers used may be rendered macroporous to improve the mass transfer.

In a further preferred embodiment, 6-aminocapronitrile is cyclized in the liquid phase with water at elevated temperatures without a catalyst by heating an aqueous solution of 6-aminocapronitrile in the liquid phase without the addition of a catalyst in a reactor to give a mixture I consisting essentially of water, caprolactam and a high-boiling fraction (high boiler).

In this preferred embodiment, an excess of water is preferably used, particularly preferably from 10 to 150, in particular from 20 to 100, mol of water per mol of 6-aminocapronitrile, to give an aqueous solution of 6-aminocapronitrile. In a further preferred embodiment, from 5 to 25 mol of water are usually used per mol of 6-aminocapronitrile, and the solution can generally be further diluted to 5–25% by weight of 6-aminocapronitrile by adding an organic solvent.

Examples of suitable solvents are:

$C_1$–$C_4$-alkanols, such as methanol, ethanol, n-propanol, isopropanol and butanols, glycols, such as ethylene glycol, diethylene glycol, triethylene glycol, tetraethylene glycol, ethers, such as methyl tert-butyl ether and diethylene glycol diethyl ether, $C_6$–$C_{10}$-alkanes, such as n-hexane, n-heptane, n-octane, n-nonane and n-decane, and cyclohexane, benzene, toluene, xylene, lactams, such as pyrrolidone and caprolactam, and N-$C_1$–$C_4$-alkyllactams, such as N-methylpyrrolidone, N-methylcaprolactam and N-ethylcaprolactam.

In a further embodiment, from 0 to 5, preferably from 0.1 to 2, % by Freight of ammonia, hydrogen or nitrogen may be added to the reaction mixture.

The reaction is preferably carried out at from 200 to 370° C., preferably from 220 to 350° C., particularly preferably from 240 to 320° C.

The reaction is usually carried out under superatmospheric pressure, the pressure chosen being as a rule from 0.1 to 50, preferably from 5 to 25, MPa, so that the reaction mixture is preferably in the liquid phase.

The duration of the reaction depends essentially on the chosen process parameters and, in the continuous process, is generally from 20 to 180, preferably from 20 to 90, minutes. As a rule, lower conversion is obtained in a shorter reaction time, and observations to date have shown that troublesome oligomers form during longer reaction times.

The cyclization is preferably carried out continuously, preferably in a tube reactor, in stirred kettles or in combinations thereof.

The cyclization may also be carried out batchwise. The reaction time is then usually from 30 to 180 minutes.

The discharge is, as a rule, a mixture consisting essentially of from 50 to 98, preferably from 80 to 95,% by weight of water and from 2 to 50, preferably from 5 to 20,% by weight of a mixture consisting essentially of from 50 to 90, preferably from 65 to 85, % by weight of caprolactam and from 10 to 50, preferably from 15 to 35, % by weight of a high-boiling fraction (high boilers).

In a further embodiment, after the partial hydrogenation and after removal of ammonia and inert compound or compounds A (bottom product of column 3), any abraded catalyst material present and high boilers are removed by evaporation or distillation, by obtaining the undesired substances as bottom product and feeding the top product to the column K4.

In a further embodiment, adiponitrile and high boilers are taken off via the bottom of column K5 and fed to stage (a). In this case, it is also possible to remove a stream from the bottom of column K5.

It is also possible to purify ADN from the side stream of column K5 in a further column.

The hexamethylenediamine obtained according to the invention can be further purified by conventional methods and used for the preparation of polymers and copolymers, such as polyamide 66.

According to the invention, a part of the process for the preparation of caprolactam from adiponitrile may also be used for the simultaneous separation of 6-aminocapronitrile and hexamethylenediamine by distillation of a mixture essentially containing these compounds, wherein (a) a mixture containing essentially 6-aminocapronitrile, hexamethylenediamine, ammonia, adiponitrile and hexamethyleneimine is subjected to a distillation to give ammonia as the top product and a bottom product I, the distillation being carried out at a bottom temperature of from 60 to 250° C. and at from 5 to 30 bar in the presence of a compound which is inert under the distillation conditions, or a mixture of inert compounds A, which boils at from 60 to 250° C. at 18 bar, and the ammonia not being completely separated off, and (b) the bottom product I, containing essentially 6-aminocapronitrile, hexamethylenediamine, adiponitrile, hexamethyleneimine, inert compound or compounds A and ammonia, the ammonia content being lower than that of the mixture used in stage (a), is subjected to a second distillation to give a mixture of the inert compound A and ammonia as the top product and a bottom product II, the distillation being carried out at a bottom temperature of from 100 to 250° C. and a pressure of from 2 to 15 bar, with the proviso that the pressures of the first and of the second column are matched with one another so that, at a bottom temperature of not more than 220° C. in each case, a top temperature of more than 20° C. is obtained, or, the condensation at the top of the second column is carried out at lower temperatures, the top product, which consists of pure or relatively highly concentrated ammonia, being recycled to the first column, or the top product of the second column is recycled to the first column or to the condenser thereof in vapor form after the pressure has been increased by means of a compressor, c) the bottom product II, containing essentially 6-aminocapronitrile, hexamethylenediamine, adiponitrile, hexamethyleneimine and inert compound or compounds A, is subjected to a distillation in a third column to give the inert compound or compounds A as the top product and a bottom product III, the distillation being carried out at a bottom temperature of from 50 to 250° C. and a pressure of from 0.05 to 2 bar, with the proviso that the inert compound or compounds A obtained as the top product are fed to the second column, and, if desired, the distillation being carried out in the presence of one or more compounds B which are inert under the distillation conditions and boil at from 20 to 250° C. at 0.3 bar, (d) the bottom product III, containing essentially 6-aminocapronitrile, hexamethylenediamine, adiponitrile, hexamethyleneimine and, if desired, inert compound or compounds B, is subjected to distillation in a fourth column to give a top product KP1, containing essentially hexamethyleneimine, if desired inert compound or compounds B, and a side stream SA1, containing essentially hexamethylenediamine, the bottom temperature of the column being from 50 to 250° C. and the pressure from 0.05 to 1.5 bar, and to give a bottom product IV, and, if desired, the column is equipped with a dividing wall in the region between feed and side take-off point (Petlyuk column), so that the hexamethylenediamine obtained is essentially free of hexamethyleneimine and inert compound or compounds B and of other low boilers, top product KP1 being fed to the third column or, if required, only some of top product KP1 being fed to the third column and the remainder being removed, and e) the bottom product IV, containing essentially 6-aminocapronitrile and adiponitrile and possibly high boilers, is subjected to a distillation in a fifth column to give 6-aminocapronitrile having a purity of at least 95% as the top product and a side stream consisting essentially of adiponitrile and a bottom product V which consists of high boilers and small amounts of adiponitrile, and, if desired, the column is equipped with a dividing wall in the region between feed and side take-off point, so that the adiponitrile obtained contains relatively small amounts of high boilers, the distillation being carried out at a bottom temperature of from 50 to 250° C. and at from 10 to 300 mbar.

The novel process has the advantage that it provides a continuous process for obtaining caprolactam starting from adiponitrile, hexamethylenediamine simultaneously being obtained.

EXAMPLES (a) Hydrogenation of adiponitrile to 6-aminocapronitrile

A tube reactor having a length of 2 m and an internal diameter of 2.5 cm was filled with 750 ml of (1534 g) of catalyst consisting of 90% by weight of CoO, 5% by weight of $Mn_2O_3$, 3% by weight of $P_2O_5$ and 2% by weight of $Na_2O$, and the catalyst was then activated in the course of 48 hours in a stream of hydrogen (500 l/h) by increasing the temperature from 30° C. to 280° C. under atmospheric pressure. After the temperature had been reduced to 45° C. (inlet) or 85° C. (outlet), a mixture of 380 g/h of adiponitrile, 380 g/h of ammonia and 500 l/h of hydrogen was fed to the reactor at 200 bar. In addition, four times the feed quantity (about 3 kg/h) was circulated for removal of heat. 70% of adiponitrile were converted under these conditions. The reaction mixture consisted of 50% by weight of ammonia, 15% by weight of ADN, 17.5% by weight of aminocapronitrile (ACN), 17.4% by weight of HMD and 0.1% by weight of other substances (ACN selectivity: 50%, ACN+HMD selectivity: >99%).

b) Working up the discharged hydrogenation mixture by distillation

The discharged hydrogenation mixture from (a) was freed from catalyst and fed to the top of a first column having two theoretical plates. 5.0 kg of ammonia were separated off with 200 ppm of ethanol via the top at 47° C. and 19 bar and used for the hydrogenation (stage (a)).

The bottom product of the first column, a reaction mixture containing ethanol and small amounts of ammonia, was fed at a bottom temperature of 180° C. to a second column having 10 theoretical plates. 1.22 kg of a mixture of 30% by weight of ammonia and 70% by weight of ethanol and traces of hexamethyleneimine (HMI), hexamethylenediamine (HMD), ACN and ADN were recycled via the top of this column, at 50° C. and 10 bar, to the first column.

The bottom product of the second column, which contained 39% of ethanol and 100 ppm of ammonia and was at 177° C., was fed to a third column having 10 theoretical plates. 3.2 kg of ethanol were taken off via the top of this column at 47° C./300 mbar and recycled to the second column.

5.0 kg of product were fed from the bottom of the third column, which was at 166° C., to a fourth column having 35 theoretical plates. 5 g of HMI containing 19% of HMD were taken off via the top of this column at 67° C./90 mbar. 1.74 kg of HMD containing 155 ppm of HMI and 100 ppm of ACN were taken off as a liquid side stream from the 30th theoretical plate of this column and removed from the process.

3.25 kg of product, consisting essentially of ACN and ADN, were removed from the bottom of the fourth column, which was at 181° C., and fed to a fifth column having 20 theoretical plates. 1.75 kg of ACN containing 185 ppm of HMD and 100 ppm of ADN were obtained via the top of this column at 20 mbar and 120° C.

1.39 kg of ADN containing 800 ppm of ACN were taken off as a vapor side stream in the lower part of the fifth column. 0.11 kg of ADN containing about 10% by weight of high boilers was taken off at 190° C. via the bottom.

(c) Cyclization of 6-aminocapronitrile to caprolactam

A solution of 2 kg of ACN (from (b)), 0.64 kg of water and 17.4 kg of ethanol was passed, at 220° C. and 70 bar and with a residence time of 15 minutes, through an oil-heated tube reactor having a length/diameter ratio of 100 and containing 4 mm titanium dioxide extrudates. The discharged reaction mixture contained 1.7 kg of caprolactam, 0.06 kg of ethyl 6-aminocaproate, 0.1 kg of 6-aminocapronitrile (determined by gas chromatography) and 0.1 kg of 6-aminocaproic acid and oligomers and polymers of caprolactam (determined by means of HPLC). 1.6 kg of caprolactam were obtained therefrom by fractional distillation.

We claim:

1. A process for the simultaneous preparation of caprolactam and hexamethylenediamine starting from adiponitrile, wherein (a) adiponitrile is partially hydrogenated to give a mixture containing essentially 6-aminocapronitrile, hexamethylenediamine, ammonia, adiponitrile and hexamethyleneimine, and (b) the mixture obtained in (a) is subjected to a distillation to give ammonia as the top product and a bottom product I, the distillation being carried out at a bottom temperature of from 60 to 250° C. and a pressure of from 5 to 30 bar in the presence of a compound A which is inert under the distillation conditions, or a mixture of inert compounds A, which boils at from 60 to 250° C. at 18 bar, and the ammonia not being completely separated off, and (c) the bottom product I, containing essentially 6-aminocapronitrile, hexamethylenediamine, adiponitrile, hexamethyleneimine, inert compound or compounds A and ammonia, the ammonia content being lower than that of the mixture used in stage (b), is subjected to a second distillation to give a mixture of the inert compound or compounds A and ammonia as the top product and a bottom product II, the distillation being carried out at a bottom temperature of from 100 to 250° C. and a pressure of from 2 to 15 bar, with the proviso that the pressures of the first and of the second column are matched with one another so that, at a bottom temperature of not more than 250° C. in each case, a top temperature of more than 20° C. is obtained, or the condensation at the top of the second column is carried out at lower temperatures, the top product, which consists of pure or relatively highly concentrated ammonia, being recycled to the first column, or the top product of the second column is recycled to the first column or to the condenser thereof in vapor form after the pressure has been increased by means of a compressor, (d) the bottom product II, containing essentially 6-aminocapronitrile, hexamethylenediamine, adiponitrile, hexamethyleneimine and inert compound or compounds A, is subjected to a distillation in a third column to give the inert compound or compounds A as the top product and a bottom product III, the distillation being carried out at a bottom temperature of from 50 to 250° C. and a pressure of from 0.05 to 2 bar, with the proviso that the inert compounds A obtained as the top product are fed to the second column, and optionally conducting the distillation in the presence of one or more compounds B which are inert under the distillation conditions and boil at from 20 to 250° C. at 0.3 bar, (e) the bottom product III, containing essentially 6-aminocapronitrile, hexamethylenediamine, adiponitrile, hexamethyleneimine, and inert compound is subjected to distillation in a fourth column to give a top product KP1, containing essentially hexamethyleneimine and a side stream SA1, containing essentially hexamethylenediamine, the bottom temperature of the column being from 50 to 250° C. and the pressure from 0.05 to 1.5 bar, and to give a bottom product IV, and optionally conducting said distillation step a in a column equipped with a dividing wall in the region between feed and side take-off point (Petlyuk column), so that the hexamethylenediamine obtained is essentially free of hexamethyleneimine and inert compound or compounds B and of other low boilers, top product KP1 being fed to the third column or, only some of top product KP1 being fed to the third column and the remainder being removed, and (f) the bottom product IV, containing essentially 6-aminocapronitrile and adiponitrile and possibly high boilers, is subjected to a distillation in a fifth column to give 6aminocapronitrile having a purity of at least 95% as the top product and a side stream consisting essentially of adiponitrile and a bottom product V which consists of high boilers and small amounts of adiponitrile, and, optionally conducting distillation step (f) in a column equipped with a dividing wall in the region between feed and side take-off point, so that the adiponitrile obtained contains relatively small amounts of high boilers, the distillation being carried out at a bottom temperature of from 50 to 250° C. and a pressure of from 10 to 300 mbar, and the resulting 6-aminocapronitrile is then cyclized to caprolactam.

2. A process as claimed in claim 1, wherein the adiponitrile from the side stream of column 5 is fed to stage (a).

3. A process for the simultaneous separation of 6-aminocapronitrile and hexamethylenediamine by distillation of a mixture containing essentially these compounds, wherein (a) a mixture containing essentially 6-aminocapronitrile, hexamethylenediamine, ammonia, adiponitrile and hexamethyleneimine is subjected to a distillation to give ammonia as the top product and a bottom product I, the distillation being carried out at a bottom temperature of from 60 to 250° C. and at from 5 to 30 bar in the presence of a compound A which is inert under the distillation conditions, or a mixture of inert compounds A, which boil at from 60 to 250° C. at 18 bar, and the ammonia not being completely separated off, and (b) the bottom product I, containing essentially 6-aminocapronitrile, hexamethylenediamine, adiponitrile, hexamethyleneimine, inert compound or compounds A and ammonia, the ammonia content being lower than that of the mixture used in stage (a), is subjected to a second distillation to give a mixture of the inert compound A and ammonia as the top product and a bottom product II, the distillation being carried out at a bottom temperature of from 100 to 250° C. and a pressure of from 2 to 15 bar, with the proviso that the pressures of the first and of the second column are matched with one another so that, at a bottom temperature of not more than 250° C. in each case, a top temperature of more than 20° C. is obtained, or, the condensation at the top of the second column is carried out at lower temperatures, the top product, which consists of pure or relatively highly concentrated ammonia, being recycled to the first column, or the top product of the second column is recycled to the first column or to the condenser thereof in vapor form after the pressure has been increased by means of a compressor, (c) the bottom product II, containing essentially 6-aminocapronitrile, hexamethylenediamine, adiponitrile, hexamethyleneimine and inert compound or compounds A, is subjected to a distillation in a third column to give the inert compound or compounds A as the top product and a bottom product III, the distillation being carried out at a bottom temperature of from 50 to 250° C. and a pressure of from 0.05 to 2 bar, with the proviso that the inert compound or compounds A obtained as the top product are fed to the second column and optionally conducting the distillation step (c) in the presence of one or more compounds B which are inert under the distillation conditions and boil at from 20 to 250° C. at 0.3 bar, (d) the bottom product III, containing essentially 6-aminocapronitrile, hexamethylenediamine, adiponitrile, hexamethyleneimine and, optionally, inert compound or compounds B, is subjected to distillation in a fourth column to give a top product KP1, containing essentially hexamethyleneimine, if desired inert compound or compounds B, and a side stream SA1, containing essentially hexamethylenediamine, the bottom temperature of the column being from 50 to 250° C. and the pressure from 0.05 to 1.5 bar, and to give a bottom product IV, and optionally conducting distillation step (d) in a column equipped with a dividing wall in the region between feed and side takeoff point (Petlyuk column), so that the hexamethylenediamine obtained is essentially free of hexamethyleneimine and inert compound or compounds B and of other low boilers, top product KP1 being fed to the third column or, if required, only some of top product KP1 being fed to the third column and the remainder being removed, and (e) the bottom product IV, containing essentially 6-aminocapronitrile and adiponitrile and possibly high boilers, is subjected to a distillation in a fifth column to give 6-aminocapronitrile having a purity of at least 95% as the top product and a side stream consisting essentially of adiponitrile and a bottom product V which consists of high boilers and small amounts of adiponitrile, and optionally conducting distillation step (e) in a column equipped with a dividing wall in the region between feed and side take-off point, so that the adiponitrile obtained contains relatively small amounts of high boilers, the distillation being carried out at a bottom temperature of from 50 to 250° C. and pressure of from 10 to 300 mbar.

4. A process as claimed in either of claim 1, wherein a mixture consisting essentially of from 1 to 70% by weight of 6-aminocapronitrile,
from 1 to 70% by weight of adiponitrile,
from 0.1 to 70% by weight of hexamethylenediamine,
from 0.01 to 10% by weight of hexamethyleneimine and
from 5 to 95% by weight of ammonia, is used in stage (b).

5. A process as claimed in claim 3, wherein a mixture consisting essentially of from 1 to 70% by weight of 6-aminocapronitrile,
from 1 to 70% by weight of adiponitrile,
from 0.1 to 70% by weight of hexamethylenediamine,
from 0.01 to 10% by weight of hexamethyleneimine and
from 5 to 95% by weight of ammonia, is used in stage (a).

6. A process as claimed in claim 1, wherein ethanol is used as the inert compound A.

7. A process as claimed in claim 1, wherein hexamethyleneimine or hexamethylenediamine is used as component B.

8. A process as claimed in claim 3, wherein ethanol is used as the inert compound A.

9. A process as claimed in claim 3, wherein hexamethyleneimine or hexamethylenediamine is used as component B.

* * * * *

UNITED STATES PATENT AND TRADEMARK OFFICE
CERTIFICATE OF CORRECTION

PATENT NO.: 6,147,208

DATED: November 14, 2000

INVENTOR(S): ACHHAMMER et al.

It is certified that error appears in the above-identified patent and that said Letters Patent is hereby corrected as shown below:

Col. 15, claim 1, line 4, "6aminocapronitrile" should be --6-aminocapronitrile--.

Col. 16, claim 3, line 40, "and pressure" should be --and a pressure--.

Col. 16, claim 4, line 42, delete "either of".

Signed and Sealed this

First Day of May, 2001

*Attest:*

NICHOLAS P. GODICI

*Attesting Officer*     *Acting Director of the United States Patent and Trademark Office*